United States Patent [19]

Salerno

[11] Patent Number: 5,025,782
[45] Date of Patent: Jun. 25, 1991

[54] ADJUSTABLE RACK AND PINION KNEE BRACE

[75] Inventor: Laurie Salerno, Rahway, N.J.

[73] Assignee: Ambulatory Traction Inc., Rahway, N.J.

[21] Appl. No.: 478,505

[22] Filed: Feb. 12, 1990

[51] Int. Cl.$^5$ .............................................. A61F 5/00
[52] U.S. Cl. ................................ 128/80 C; 128/80 R; 128/77; 623/39
[58] Field of Search ................. 128/80 R, 80 C, 80 F, 128/80 H, 84 R, 84 C, 85, 87 R, 88, 77, 165; 2/22, 24; 623/39

[56] References Cited

U.S. PATENT DOCUMENTS

| | | |
|---|---|---|
| 3,827,431 | 8/1974 | Pecorella ............................ 128/80 F |
| 4,409,971 | 10/1983 | Guerriero . |
| 4,487,222 | 12/1984 | Feanny et al. . |
| 4,643,177 | 2/1987 | Sheppard et al. . |
| 4,665,905 | 5/1987 | Brown . |
| 4,732,143 | 3/1988 | Kausek et al. . |
| 4,793,333 | 12/1988 | Marquette . |

Primary Examiner—Richard J. Apley
Assistant Examiner—Lynne Reichard
Attorney, Agent, or Firm—Marvin A. Naigur

[57] ABSTRACT

A knee brace is provided with support members that are securely fastened to the thigh and calf of the wearer. A pair of rigid arms, which are pivotally connected together are mounted on the support members on opposite sides of the knee joint, such that the support members after being attached to the leg can be spread apart with respect to the rigid arms.

18 Claims, 4 Drawing Sheets

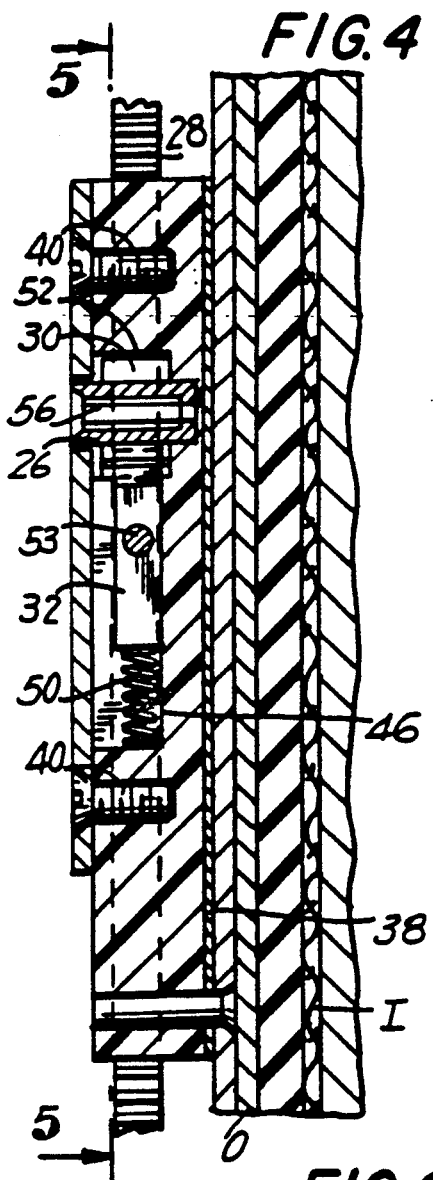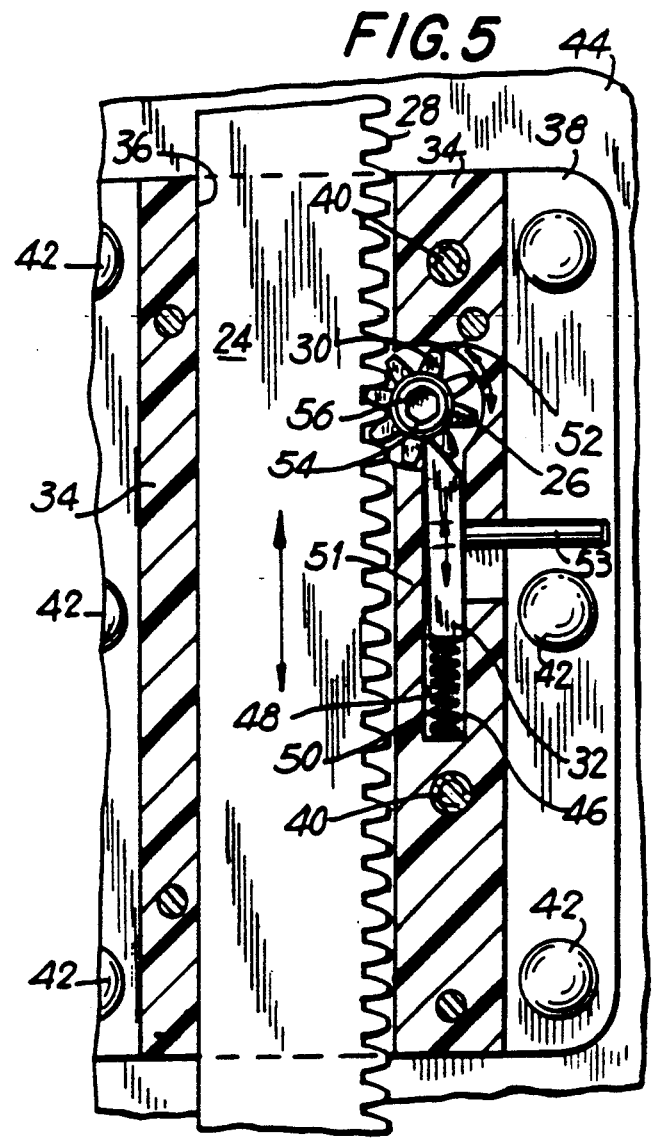

ADJUSTABLE RACK AND PINION KNEE BRACE

BACKGROUND OF THE INVENTION

The present invention relates to an apparatus for alleviating problems associated with deterioration of the knee joint through disease and injury, and more particularly to a knee brace capable of spreading apart the constituents of the knee joint, while the weight of the wearer is transferred from the thigh to the calf, such that an appreciable portion of the weight load by-passes the knee joint.

It can be well appreciated that severe problems are associated with deterioration of the cartilage in the knee joint. Since the cartilage serves as a means of cushioning and stabilizing the end of tibia and femerul bones in the knee joint, when the cartilage become damaged through trauma or disease, the ends of the bones will rub together causing pain and restriction of movement in the knee joint. With the increasing popularity of contact sports and also the prevalence of accidental bodily injuries, damaged cartilage has become a problem.

Although many different types of knee braces have heretofore been developed to compensate for injury to the knee joint, most of these braces have been designed to compensate for ligament damage. Particularly in the sports area, the knee braces have been geared to allow an athlete to be able to run and again participate in their sport, notwithstanding a permanent and irrepairable injury to the knee joint. However, much less attention has been given to individuals with cartilage damage, which in many instances is severely debilitating enough to prevent normal walking. Also, in some instances the damage to the knee joint may be severe enough, to warrant complete surgical removal of the diseased or injured knee joint, and replacement with an artificial prosthetic knee joint.

In accordance with the present invention it is possible to achieve normal movement in cases of damaged knee joints, and also alleviate the pain caused by bone contact in the joint area. This is achieved by an external mechanical brace which is provided with a pivotal hinge located on either side of the knee joint and the ends of the brace are respectively secured to the thigh and calf, such that the brace can be tightly attached for prolonged periods of time without interfering with and restricting the blood circulation in the outer epidermal areas of the skin of the wearer which is coextensive with the brace material. The means for securing the brace to the thigh and skin allow a sufficient tight fit, such that additional means can be provided to adjustably spread apart the two principal elements of the knee brace in accordance with the comfort level of the individual wearer. The synergistic effect, of separating the bones, which came together at the knee joint together with the transfer of the weight from the thigh to the calf, while by-passing the knee joint, results in a marked improvement in the mobility of the wearer.

SUMMARY OF THE INVENTION

In accordance with an illustrative embodiment demonstrating features and advantages of the present invention, there is provided an apparatus for bracing the knee joint of a wearer. First and second support members are securely mounted respectively on the thigh and calf of the wearer. A pair of first arms and second arms are respectively mounted on the first and second support members. Pivotal connections are provided between the adjacent free ends of the first and second members. It is preferable to provide a rack-and-pinion sliding connection at each location where the arms are mounted on the support members. Thus, in accordance with the present invention, it is possible to adjustably spread apart the support elements in relation to their respective arms. In this manner, the weight of the wearer is transferred through the arms, thereby by-passing the knee joint of the wearer. Accordingly, a salutary effect during movement of the knee joint is achieved by separating the contiguous bone structure in the joint and also alleviating the stress to the knee joint caused by the weight load of the wearer.

BRIEF DESCRIPTION OF THE DRAWINGS

The above brief description, as well as further objects, features, and advantages of the present invention, will be more fully appreciated by reference to the following detailed description of presently preferred but nonetheless illustrative embodiments in accordance with the present invention, when taken in connection with the accompanying drawings wherein:

FIG. 4 is a sectional view of the rack-and-pinion mechanism shown in FIG. 3, taken in the section of the arrows 4—4;

FIG. 5 is an enlarged elevational view of the rack-and-pinion mechanism shown in FIG. 1, with the outermost parts removed to better show the internal elements;

FIG. 6 is a side elevational view of the knee brace shown in FIG. 1, but reduced in size to show the knee in the flexed position;

FIG. 7 is an enlarged view of a portion of the knee brace shown in FIG. 6, with an alternate embodiment of the invention shown which incorporates an air bag for obtaining a more secure and tight fit between the support elements and the leg of the wearer;

DESCRIPTION OF THE PREFERRED EMBODIMENTS

Figure 1:
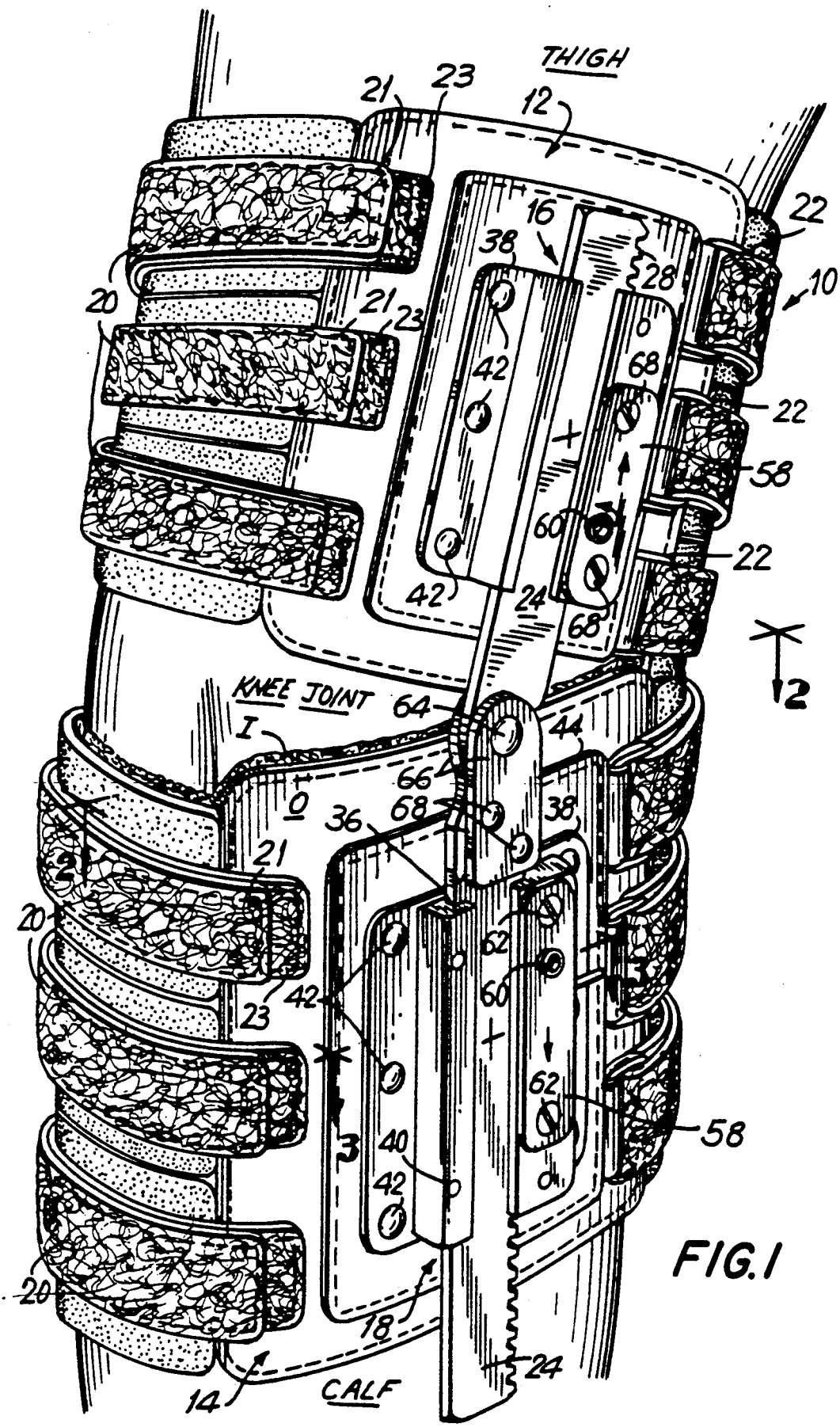
FIG. 1 is an elevational view showing the knee brace of the present invention mounted on the knee of the wearer.

With reference to FIGS. 1 and 6, a knee brace, generally referred to by the reference numeral 10, is mounted at a location above and below the knee of the wearer on the thigh and calf, respectively. An upper support member 12 is securely fastened to thigh and a lower support member 14 is securely fastened to the calf. A pair of upper sliding assemblies 16 and a pair of lower sliding assemblies 18 are respectively mounted on the upper support member 12 and lower support member 14. As will hereafter be more fully described, in addition to the metallic components, the knee brace 10, is fabricated from leather and velcro material, as well as special fabric material that allows for the support members 12 and 14 to be securely fastened to the thigh and calf, for extended periods of time without inhibiting the circulation in the underlying skin areas.

Figure 2:
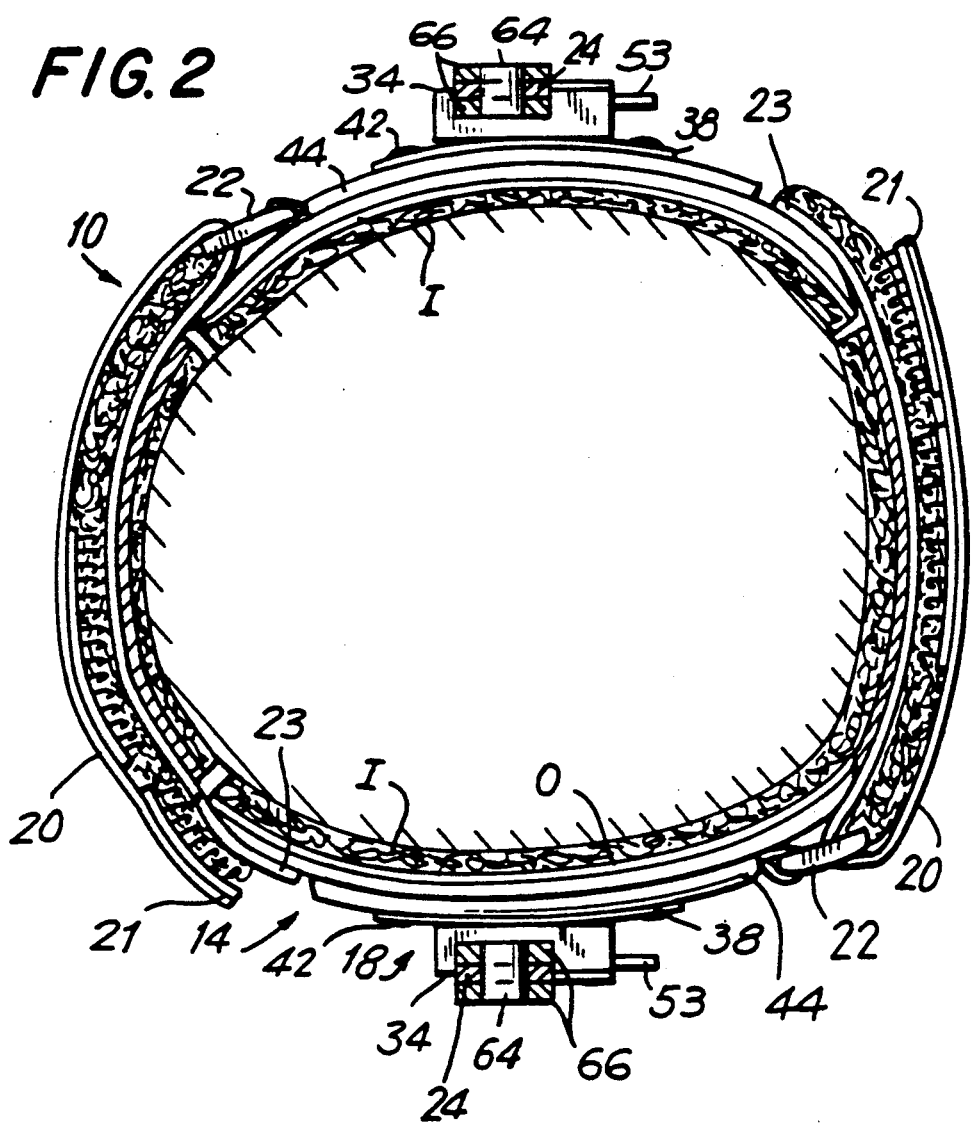
FIG. 2 is a sectional view of the knee brace shown in FIG. 1 taken in the direction of the arrows 2—2, to better show the fabric composition of the support structure.
Figure 3:
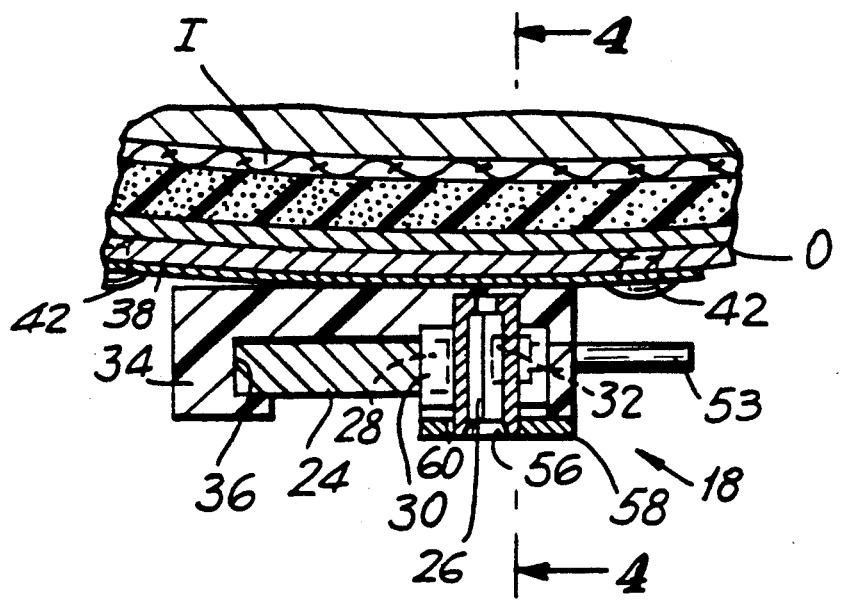
FIG. 3 is an enlarged sectional view of the rack-and-pinion mechanism shown in FIG. 2.

By progressively inspecting FIGS. 1 and 2, it can be appreciated that the support members 12 and 14 are fabricated from an outer covering designated by the letter O which overlays a coextensive inner lining designated by the letter I. The inner lining I is preferably fabricated from fabric with perforated openings, such that the inner lining I forms a padded interface between the outer covering O and the skin of the wearer. In this manner, the outer covering O and inner lining I form a sheath of fabric capable of being entrained around the thigh and calf of the wearer. The perforated fabric of the inner lining I allows for the support members 12, 14 to be tightly fastened around the thigh and calf, respectively, without interfering with the proper circulation of the underlying skin.

Figure 8:
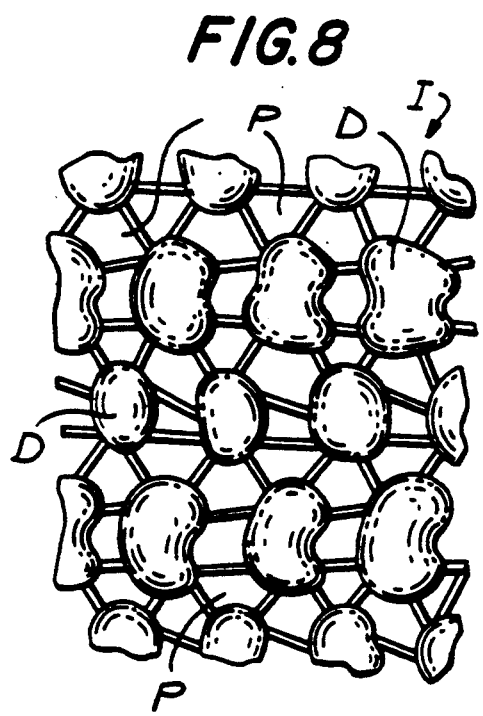
FIG. 8 is an enlarged view of the inner lining fabric.

It should be appreciated that alternate materials can be used in the fabrication of the inner lining I and outer covering O. As best shown in FIG. 8, the inner lining I is formed with a coating of plastic, such as polyvinyl chloride, over fabric material, with perforations P, and raised dimples D. An alternate material used for the inner lining I, could include a heavier material such as sheep skin. By providing the proper type of inner lining I in accordance with the present invention, the support members 12, 14 can be sufficiently tightened about the leg of the wearer, such that a streching of the underlying skin occurs when the support members 12, 14 are spread apart. In this manner, it is possible to obtain extended period of use of the knee brace 10 by the wearer.

The outer covering O can be produced from natural materials such as leather or a composite synthetic fabric, which would comprise a foam central core with an outer overlying layer of material of synthetic fabric such as either Dupont Antron ® or Lycra ® or Spandex ® and an inner layer of synthetic material such as Dupont Nylon Tricote ®. This composite synthetic material could be used with or without the inner lining I.

It is essential that the support member 12, 14 be tightly secured above and below the knee joint, and this is accomplished by providing clamping straps 20, secured along one vertical edge of the support member 12 and 14, which are trained through clamping loops 22 mounted on upper sliding arm assembly 16 and lower sliding assembly 18. It can be appreciated that the construction of the upper support member 12 is substantially the same as the lower support member 14, except for the size configuration, which is in accordance with the overall shape of the thigh and calf of the wearer. The clamping straps 20 and loops 22, allow for adjusting the tightness of the support members 12 and 14 in accordance with the leg size of a specific individual wearer. This is achieved by providing an adjustable fastening device between the free vertical edges of the support members 12 and 14. As best seen in FIG. 1, the fastening device for the knee brace is obtained through providing velcro material at both the free ends 21 and secured ends 23 of a total as six sets at clamping straps 20.

In the preferred embodiment of the knee brace 10 of the present invention, the upper sliding assemblies 16 and lower sliding assemblies 18 are provided with identical sliding mechanisms, as it has been found that this affords the most optimum and comfortable use for the wearer. However, either the upper sliding assembly 16 or lower sliding assembly 18 could be replaced by a fixed, non-sliding arm, such that sliding adjustment could only be accomplished through either the thigh or calf of the wearer.

Since the upper sliding assembly 16 and lower sliding assembly 18 are identical, the same reference numerals will be used to designate like components. Accordingly, the sliding assemblies 16 and 18 which are best shown in FIGS. 4 and 5, are comprised of a rack arm 24, which meshes with a pinion 26. The rack arm 24 is formed with gear teeth 28, and the pinion 26 is formed with gear teeth 30 for meshing with the gear teeth 28, as well as with a pawl 32. The sliding assemblies 16 and 18 also include a pair of groove arms 34 which are spaced apart from each other to form a keyway 36 for slidably receiving the rack arm 24. The groove arms 34 are mounted onto a metal base plate 38 by means of set screws 40, and the base plate is secured by rivets 42 to a leather mounting pad 44, that is stitched onto the support members 12, 14. As shown in FIG. 5, the groove arm 34 adjacent the gear teeth 28 is formed with an internal housing 46 which includes, a machined cylindrical chamber 48 for receiving a compression spring 50 and the pawl 32, and a circular chamber 52 is in communication with the cylindrical chamber 48. The internal housing 46 is also provided with a clearance opening for receiving a flat disc 51 and release lever 53 which passes through and is mounted in opening on the pawl 32. The pinion 26 is mounted in the circular chamber 52 on a shaft 54 which rotates in a bore formed in the groove arm 38. The shaft 54 is provided with a hexagonal indentation 56 at its outermost end for receiving an allen wrench for rotating the pinion 26 in both a clockwise and counterclockwise direction as shown by the bi-directional arrow in FIG. 5. The pawl 32 is formed with an angular free end, sized to smoothly mesh with the gear teeth 30. The compression spring 50 urges the pawl in a direction towards the pinion 26 and prevents further longitudinal movement of the groove arm 34. By pressing the release lever 53 in a direction toward the knee joint, the pinion 26 can be rotated freely. A cover plate 58 with an opening 60, for allowing access to shaft 54, is mounted on the groove arm 34 by means of screws 62, which allow free access to the internal housing 46. The rack arms 24 are pivotly connected at opposite sides of the knee joint, at their adjacent free ends by pivot point pins 64. This is achieved by securing a pair of mounting brackets 66, by means of rivets 68, on the lower sliding assembly 18. The pivot point pin 64 is mounted through a pair of aligned openings formed in mounting brackets 66 and an aligned opening in rack arm 24, of upper sliding assembly 16, such that rack arms 24 of adjacent upper sliding assembly 16 and lower sliding assembly 18 can pivot freely about the axis of pivot point pin 64. The pivoting of rack arms 24 about pin 64 allow for free extension and retraction of the calf of the wearer, and also serves to prevent tortional twisting of the calf about the knee joint, such that knee ligament strain and injury can be alleviated.

Figure 9:
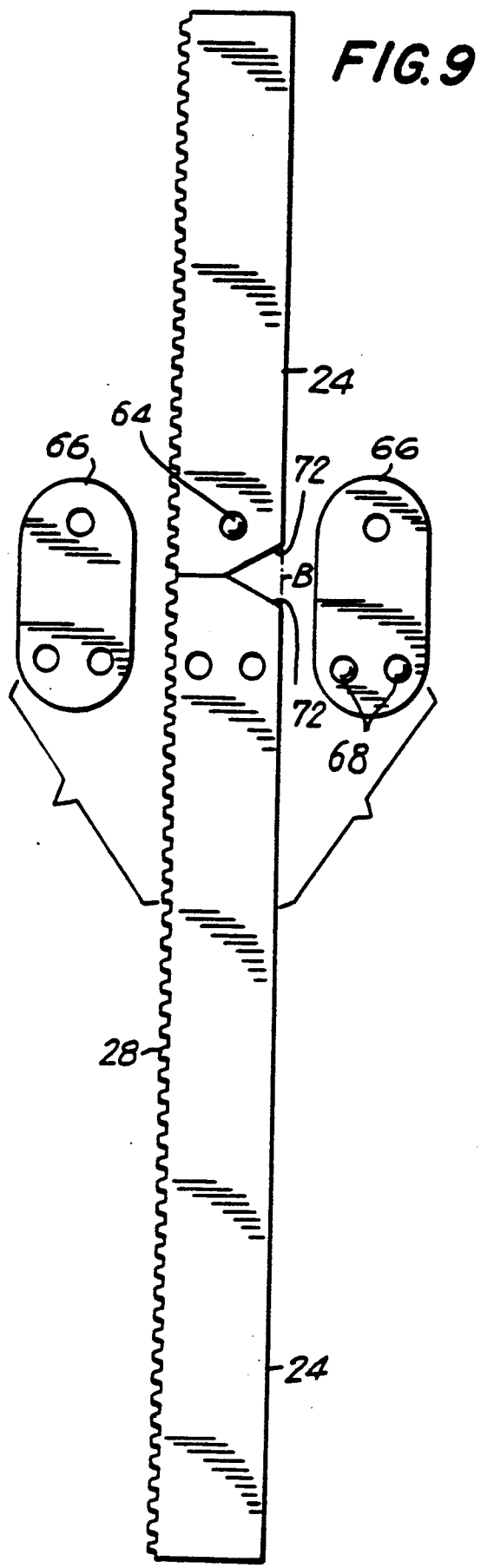
FIG. 9 is an enlarged sectional view of the rack-and-pinion mechanism arms in an unassembled position.

Turning to FIG. 9, the rack arms 24 are shown in an unassembled position but aligned in the actual fully assembled position. Thus, it can be seen that adjacent ends of the rack arms 24 are formed with forward stop edges 70 and reward stop edges 72. The forward stop edges 70 are substantially flat and transverse to the longitudinal axis of the rack arms 24, whereby rack arms 24 are prevented from moving beyond the normally fully extended position of the knee joint when the adjacent stop edges 70 come together in an abutting and coextensive position. The reward stop edges 72 of adjacent rack arms 24 diverge outwardly to form a triangle with a base designated B. As the dimension of B is increased, the rack arms 24 are allowed to achieve a greater degree of reward retraction. The maximum reward retraction of the rack arms 24 is obtained when the reward stop edges 72 come together in an abutting and coextensive position.

Figure 10:
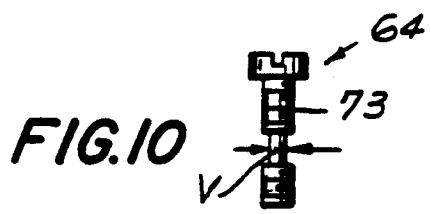
FIG. 10 is a sectional view of the variable diameter pivot.

As shown in FIG. 10 the pivot point pin 64 comprises a variable diameter screw 73, in which the diameter V can be varied by providing different sized screws 73. By decreasing the diameter D, it is possible to increase the degree of maximum reward retraction of rack arm 24, as the threads provided on either side of the diameter V, can easily be threadably engaged with the mounting brackets 66.

In mounting the knee brace 10 on the leg of the wearer, it may be necessary to provide supplemental means for tightly securing the upper support member 12 to the thigh. In accordance with an alternate embodiment of the present invention, additional mounting pressure between the thigh of the wearer and interface with upper support member 12 is achieved through the provision of a removable air bladder 74. As shown in FIG. 7, the removable air bladder 74 is provided with a small removable hand pump 76 in flow communication with the bladder 74 through tubing 78 with a check valve 80. The bladder 74 is preferably placed on the side of the thigh of the wearer and inflated by squeezing the hand pump 76 until the upper support member is securely mounted in a comfortable manner, at which point the check valve 80 is closed and the hand pump 76 is removed.

In commencing the normal use of knee brace 10, it can be appreciated that the knee brace 10 can either be stored in a completely flat position with the clamping straps 20 unthreaded from the loops 22 or with the clamping straps 20 in the loops 22, but spread apart for easily slipping the knee brace 10 over the leg of the wearer. In either storage mode, the knee brace can easily be placed on the leg of the wearer in the position substantially as shown in FIG. 1. The clamping straps 20, are secured and the air bladder 74 can be used to obtain supplemental tightening of the upper support member 12. In the preferred installation mode of the knee brace 10, the lower support member 18 is moved downwardly with respect to the knee joint by rotating the allen wrenches in the hexagonal indentations 56 located at opposite sides of the calf. By rotating both of the allen wrenches in unison in a clockwise direction on the lower assembly 18, the pinions 26 slide the lower assembly 18 downwardly, and the knee joint is maintained in a stretched-apart position through the pawl 32 engaging the gear teeth 30 to prevent counterclockwise rotation of the pinion 26. The above procedure can then be applied in the adjustment of the upper sliding assembly 16, except that the allen wrenches would have to be rotated in counter clockwise direction to obtain the same spreading apart at the location of the knee joint. When it becomes necessary to release this spreading-apart pressure, this can be accomplished by moving any one or all of the four release levers 52 in the direction of the knee joint. The release levers 52 can either be moved in a gentle manner to click one or two gear teeth 30 at a time to partially release the pressure or held down to disengage the pawl 32 and completely release the pressure.

By obtaining superior gripping of the support member 12, 14 through the inner lining I, including the stretching action of the skin, during the spreading apart of the knee joint, it is possible to exert relatively less tension through the clamping straps 22. In this manner, adequate compression of the skin underlying the free ends of the rack arms 24 is achieved, such that stretching of the skin occurs during the spreading apart of the knee joint. Furthermore, the stretching action to the underlying skin allows the upper support member 12 and lower support member 14 not to slip along the skin during long periods of use by the wearer. This allows for a minimum degree of compressive force required through the clamping straps 20, and the attendant blood circulation problems associated with too much compressive force will be alleviated. By using the elasticity of skin to maintain tractive force with the knee brace 10 is in the spread-apart position, it is possible to achieve ambulatory traction.

From the foregoing, it can be appreciated that in accordance with the present invention, applicant has provided a knee brace 10 which allows a stretching apart of the calf with respect to the thigh along the longitudinal axis of the leg, while continuing to maintain pivotal movement at the knee joint. This allows a substantial part of the load created by weight of the wearer to pass from the upper sliding assembly 16 through the pivot point 64 to the lower sliding assembly 18, and tortional or twisting of the leg about the knee joint is prevented. This by-passing of a substantial portion of the weight load from being transmitted through the knee joint, results in relieving the stress to the knee joint associated with normal ambulatory motion. In particular, the present invention is helpful to individuals with cartilage or ligament damage or injury to the knee.

Additional modifications, changes and substitutions are intended in the foregoing disclosure, and, in some instances, some features of the invention will be employed without corresponding use of other features. Accordingly, it is appropriate that the appended claims be construed broadly and in a manner consistent with the spirit and scope of the invention herein.

What is claimed is:

1. Apparatus for bracing the knee joint of a wearer comprising:
   a first support member securely fastened to the thigh of the wearer;
   a second member securely fastened to the calf of the wearer;
   a pair of first arms mounted on said first support member;
   a pair of second arms mounted on said second member;
   means connected between the free ends of said first arms and second arms for pivotally mounting said first arms to said second arms; and means on at least one of said supports member for spreading apart the support member longitudinally in relation to the arm members into a fixed position on the arm member (moveably connecting the support of said arms members for spreading apart said support members in relation to the respective arms), such that the load created by the weight of the wearer is transferred through said arms from the first support member to the second support member, and the knee joint is by-passed by a substantial portion of said load.

2. Apparatus for bracing the knee joint of a wearer according to claim 1, in which said first support member and said second support member, each include a sheath of fabric material entrained around the longitudinal axis of the leg of the wearer.

3. Apparatus for bracing the knee joint of a wearer according to claim 2, in which elongated straps are provided having one end attached to said sheath of fabric material and the other free end wound around the leg of the wearer, and attachment means between said free end and said sheath for tightly securing the support members to the thigh and calf of said wearer.

4. Apparatus for bracing the knee joint of a wearer according to claim 3, in which an underlying layer of fabric formed with perforations is fastened to said sheath in a position coextensive with the bottom of said sheath and the skin of the wearer, such that tightening of said straps will not impede the blood circulation of the wearer.

5. Apparatus for bracing the knee joint of a wearer according to claim 1, in which said first arm and second arm include elongated racks formed with gear teeth, said means for movably connecting said support members including pinions formed with gear teeth for engaging the gear teeth of said rack, and said pinions mounted on the support members such that rotation of said pinions towards each other will cause said support members to spread apart.

6. Apparatus for bracing the knee joint of a wearer according to claim 5, in which said means connected between the arms of said support members comprises said first and second arms formed with aligned bores, and a pin inserted through said bores for pivotally mounting in said second arms to said first arms, such that said knee joint is free to achieve pivotal movement of said calf and prevent tontional rotation of said calf with respect to said knee joint.

7. Apparatus for bracing the knee joint of a wearer comprising:
   a first support member securely fastened to the thigh of the wearer;
   a second support member securely fastened to the calf of the wearer;
   a pair of first arms mounted on said first support member;
   a pair of second arms mounted on said second member;
   means connected between the free ends of said first arms and second arms for pivotally mounting said first arms to said second arms; and
   a pair of rack arms formed with gear teeth mounted on at least one of said pairs of support members and a circular gear formed with gear teeth for obtaining gear meshing engagement between said gear teeth, such that rotation of said circular gear imparts sliding movement to said support members in relation to the respective arms to spread apart said support members, whereby the load created by the weight of the wearer is transfered through the arms from the first support member to the second support and the knee joint is by-passed by a substantial portion of said load.

8. Apparatus for bracing the knee joint of a wearer according to claim 7, in which said means connected between the arms of said support members comprises said first and second arms formed with aligned bores, and a pin inserted through said bores for pivotally mounting in said second arms to said first arms, such that said knee joint is free to achieve pivotal movement of said calf and prevent tortional rotation of said calf with respect to said knee joint.

9. Apparatus for bracing the knee joint of a wearer according to claim 7, in which said first support member and said second support member, each include a sheath of fabric material entrained around the longitudinal axis of the leg of the wearer.

10. Apparatus for bracing the knee joint of a wearer according to claim 9, in which elongated straps are provided having one end attached to said sheath of fabric material and the other free end wound around the leg of the wearer, and attachment means between said free end and said sheath for tightly securing the support members to the thigh and calf of said wearer.

11. Apparatus for bracing the knee joint of a wearer according to claim 10, in which an underlying layer of fabric formed with perforations is fastened to said sheath in a position coextensive with the bottom of said sheath and the skin of the wearer, such that upon spreading apart said support members said layer of fabric will grip and stretch the skin and said straps can be sufficiently tightened so as to not impede the blood circulation of the wearer.

12. Apparatus for bracing the knee joint of a wearer according to claim 11, in which a bladder capable of being inflated with air is placed between said layer of fabric and skin such that inflation of said bladder will impart additional tightening of said sheath with respect to the leg of the wearer.

13. Apparatus for bracing the knee joint of a wearer according to claim 12, in which a removeable pump is provided for inflating said bladder.

14. Apparatus for bracing the knee joint of a wearer according to claim 10, in which said underlying layer of fabric material is formed from sheepskin.

15. Apparatus for bracing the knee joint of a wearer according to claim 10, in which said underlying layer of fabric material includes cloth material coated with polyvinyl chloride and formed with dimples between said perforations.

16. Apparatus for bracing the knee joint of a wearer according to claim 9, in which said sheath of fabric material is formed from leather.

17. Apparatus for bracing the knee joint of a wearer according to claim 7, in which a pair of rack arms formed with gear teeth are mounted on said first support member and a pair of rack arms formed with gear teeth are mounted on said second support member.

18. Apparatus for bracing the knee joint of a wearer according to claim 7 or claim 8, in which the ends of said rack arms adjacent said pins are formed with stop edges that are conformed to limit the degree of forward and rearward pivotal movement of each of the pivotal rack arms.

* * * * *